United States Patent [19]

Dusing

[11] Patent Number: 5,474,894
[45] Date of Patent: Dec. 12, 1995

[54] IMMUNODEFICIENCY VIRUS NEUTRALIZATION ASSAY

[75] Inventor: Sandra K. Dusing, Knoxville, Md.

[73] Assignee: Quality Biological, Inc., Gaithersburg, Md.

[21] Appl. No.: 183,767

[22] Filed: Jan. 21, 1994

[51] Int. Cl.$^6$ ..................................................... C12Q 1/70
[52] U.S. Cl. ..................... 435/5; 435/240.1; 435/240.2; 435/240.21; 435/974
[58] Field of Search ........................... 435/5, 974, 240.1, 435/240.2, 240.21

[56] References Cited

U.S. PATENT DOCUMENTS

| | | | |
|---|---|---|---|
| 5,140,405 | 8/1992 | Ohno | 530/350 |
| 5,180,660 | 1/1993 | Ohno | 435/5 |
| 5,217,895 | 6/1993 | Ohno | 435/240.27 |

FOREIGN PATENT DOCUMENTS

WO93/19786  10/1993  WIPO.

OTHER PUBLICATIONS

World Health Organization Global programme on AIDS, "Report of a WHO workshop on the measurement and significance of neutralizing antibody to HIV and SIV London, 3–5 Oct. 1988", AIDS, vol. 4, pp. 269–275 (1990).
Mitsuya et al. "Protection of T Cells against Infectivity and Cytopathic Effect of HTLV–III in Vitro." in: Miwa et al, *Retroviruses in Human Lymphoma/Leukemia* (Japan Sci. Soc. Press Tokyo/UNU Science Press, Utrecht, 1985), pp. 277–288.
Sandström et al. "Antiviral Therapy in AIDS: Clinical Pharmacological Properties and Therapeutic Experience to Date." Drugs, vol. 34 (1987), pp. 372–390.
Tsunetsugu–Yokota et al, Journal of Virological Methods, vol. 41, pp. 47–58 (1993).
Von Gegerfelt et al, Virology, 185, pp. 162–168 (1991).
Burns et al, AIDS Research and Human Retroviruses, vol. 8, No. 6, pp. 1189–1192 (1992).
D'Souza et al, AIDS, vol. 5, No. 9, pp. 1061–1070 (1991).
Report of a WHO workshop . . . HIV and SIV, London, 3–5 Oct. 1988; AIDS, vol. 4, No. 3, pp. 269–275 (1990).
Vujcic et al, AIDS Research and Human Retroviruses, vol. 6, No. 7, pp. 847–853 (1990).
Kliks et al, Proc. Natl. Acad. Sci. USA, vol. 90, pp. 11518–11522 (1993).
Homsy et al, Journal of Virology, vol. 64, No. 4, pp. 1437–1440 (1990).
Cheng–Mayer et al, Proc. Natl. Acad. Sci. USA, vol. 85, pp. 2815–2819 (1988).
Ho et al, Journal of Virology, vol. 61, No. 6, pp. 2024–2028 (1987).
Javaherian et al, Proc. Natl. Acad. Sci. USA, vol. 89, pp. 1418–1422 (1992).
Broliden et al, Proc. Natl. Acad. Sci. USA, vol. 89, pp. 461–465 (1992).
Welch et al, Journal of Clinical Microbiology, vol. 30, No. 6, pp. 1424–1427 (1992).
Skinner et al, Journal of Virology, vol. 62, No. 11, pp. 4195–4200 (1988).
White–Scharf et al, Virology, 192, pp. 197–206 (1993).
Potts et al, Virology, 197, pp. 415–419 (1993).
Aids Research and Human Retroviruses, vol. 9, No. 6, pp. 501–504 (1993).
Albert et al, AIDS, vol. 4, No. 2, pp. 107–112 (1990).

*Primary Examiner*—Michael P. Woodward
*Assistant Examiner*—Jeffrey Stucker
*Attorney, Agent, or Firm*—Birch, Stewart, Kolasch & Birch

[57] ABSTRACT

A method for assaying the ability of an antibody to neutralize primary clinical isolates of human immunodeficiency virus (HIV) in primary human lymphocytes comprising the steps of contacting primary human lymphocytes with HIV and an antibody sample to be tested, without preincubating the antibody sample and the virus, culturing the primary human lymphocytes under conditions which allow for HIV replication without removal of the virus inoculum or antibody samples to be tested, and measuring HIV replication in the primary human lymphocytes by one or more of several conventional methods.

19 Claims, No Drawings

IMMUNODEFICIENCY VIRUS NEUTRALIZATION ASSAY

This invention was made with U.S. Federal Government support under Contract No. NO1-AI-05084 awarded by the National Institute of Allergy and Infectious Diseases (NIAID). The Government has certain rights in the invention.

BACKGROUND OF THE INVENTION

1. Field of the Invention

The present invention is directed to an in vitro immunodeficiency virus neutralization assay.

2. Description of Related Art

In order to develop useful vaccines, drugs and other therapeutic agents for treating and/or preventing human immunodeficiency virus (HIV) infections in humans, it is very useful to evaluate these vaccines, drugs and therapeutic agents in a cell culture (in vitro) system to determine their ability to inhibit or interfere with viral replication. In this respect, there has been a considerable amount of work with antibodies which are reactive with antigens present in or on HIV. These antibodies may arise as a result of HIV infection and, thus, are diagnostic of this infection or these antibodies may be elicited by exposure to candidate HIV vaccines and, thus, may predict protection from future infection or prevention of disease progression. In the past, these antibodies have usually been evaluated in an in vitro cell culture system which utilizes a continuous cell line, Potts et al, Virology, 197, 415–419(1993), White-Scharf et al, Virology, 192, 197–206(1993), Ho et al, J. Virol. 61, 2024–2028(1987), Javaherian et al, PNAS USA, 89, 1418–1422(1992), Broliden et al, PNAS USA, 89, 461–465(1992), Welch et al, J. Clin. Microbiol., 30, 1424–1427(1992) and Skinner et al, J. Virol., 62, 4195–4200(1988). In these most commonly used known systems, the antibody sample to be tested and the virus are mixed with each other and incubated for a period of time (usually one hour or more) and the antibody/virus mixture is then added to the cells. However, a continuous cell culture system is not an ideal system for predicting the effectiveness of an antibody in preventing HIV replication in vivo since there are numerous biological and physiological differences between the highly selected and potentially transformed cells which make up a continuous cell line and the normal cells which are present in the human body.

There have been several reports for measuring the ability of anti-HIV antibodies to neutralize laboratory strains and clinical isolates of HIV using primary human lymphocytes, also referred to as peripheral blood mononuclear cells (PBMC), Kliks et al, PNAS USA 90, 11518–11522(1993), Albert et al, Aids Res. Human Retroviruses, 9, 501–514(1993), Albert et al, AIDS 4, 107–112(1990), Cheng-Mayer et al, PNAS USA, 85, 2815–2819(1988) and Homsy et al, J. Virol., 64, 1437–1440(1990). Laboratory strains of HIV are different from primary clinical isolates of HIV in that they have been adapted via mutation to replicate in continuous lymphocytic cell lines. There are limited published reports of neutralization of clinical HIV isolates in peripheral blood mononuclear cells. In all these assays, the laboratory strains and clinical isolates of HIV and antibody samples were preincubated for a period of time prior to addition to the target peripheral blood mononuclear cells. In addition, the clinical HIV isolates used in all studies except one, Albert et al, AIDS, 4, 107–112(1990) had been passaged in the laboratory since initial isolation in 1984 and 1985, Levy and Shimabukuro, J. Infect. Dis., 152, 734–738(1985), Levy et al, Science, 225, 840–842(1984), and Levy et al, Lancet, 11, 586–588(1985) and, thus, cannot be considered to be primary isolates of HIV.

SUMMARY OF THE INVENTION

For the reasons discussed above, it is desirable to develop an assay for HIV neutralizing antibody samples which is a better model for predicting the efficacy of antibodies for neutralizing primary HIV clinical isolates in vivo. In addition, such an assay could be used with known and previously characterized HIV neutralizing antibodies to identify and serotype unknown primary clinical isolates of HIV. Six major subtypes of HIV, A–F, have been identified by DNA sequence analysis of the viral envelope gene and have been related to distinct geographical regions, Meyers et al, Los Alamos Natl. Lab., Human Retroviruses and AIDS Database. All isolates from North America and Europe belong to subtype B.

In its broadest aspect, the assay comprises contacting primary lymphocytes with immunodeficiency virus and an antibody, without preincubating the antibody sample and said immunodeficiency virus, culturing said primary lymphocytes under conditions which allow for immunodeficiency virus replication, and measuring immunodeficiency virus replication in said primary lymphocytes.

When the assay is used to determine the ability of an antibody sample to neutralize immunodeficiency virus, the assay comprises the steps of contacting primary human lymphocytes with HIV and an antibody sample to be tested, without preincubating said HIV and said antibody sample, culturing said primary human lymphocytes under conditions which allow for HIV replication, and measuring HIV replication in said primary human lymphocytes. The assay is preferably an assay for determining the ability of an antibody sample to neutralize primary clinical isolates of human immunodeficiency virus which comprises the steps of contacting primary human lymphocytes with HIV and an antibody sample to be tested without a significant amount of pre-incubation of the antibody sample and the virus, culturing the primary human lymphocytes in the continuous presence of both the virus inoculum and the antibody sample to be tested under conditions which allow for HIV replication, and measuring HIV replication in the primary human lymphocytes.

When the assay is used to identify and/or serotype an unknown isolate of HIV, the assay comprises the steps of contacting primary human lymphocytes with said HIV and a known antibody, without preincubating said HIV and said antibody, culturing said primary human lymphocytes under conditions which allow for HIV replication, and measuring HIV replication in said primary human lymphocytes.

In another preferred embodiment, the assay comprises the steps of mixing HIV and an antibody together and maintaining the resulting mixture at a temperature less than 6° C. and for a time of less than 15 minutes, contacting primary human lymphocytes with the mixture of HIV and an antibody and continuously mixing the primary human lymphocytes, antibody and HIV for at least 45 minutes to allow for adsorption between said primary human lymphocytes, said HIV and antibody, culturing said primary human lymphocytes under conditions which allow for HIV replication, without washing said primary human lymphocytes, and measuring HIV replication in said primary human lymphocytes.

It has been discovered that if the antibody sample to be tested and the HIV are mixed together without preincubation prior to adding these materials to the primary human lymphocytes and, subsequently, the unadsorbed virus and residual antibody sample is not removed following a period of virus adsorption, it is possible to easily differentiate antibody samples which are very effective in neutralizing HIV from antibody samples which are not very effective in neutralizing HIV. In summary, the procedures used to obtain results in a continuous cell culture system with laboratory strains of HIV do not correlate well with the procedures required to obtain results in the primary human lymphocyte system using primary clinical isolates of HIV in regard to preincubation of the HIV with the antibody sample and removal of the antibody and HIV inoculum following virus adsorption.

DETAILED DESCRIPTION OF THE INVENTION

The cells used in the assay of the present invention are primary lymphocytes (peripheral blood mononuclear cells), preferably primary human lymphocytes, which are separated from samples of whole blood from HIV seronegative donors as soon as possible after being obtained from donors. The lymphocytes are separated by standard density gradient centrifugation procedures using commercially available separation medium. The cells should be incubated at 37° C. in a humidified $CO_2$ atmosphere in RPMI 1640 medium (Quality Biological, Inc.) with 10% fetal bovine serum (FBS), or FBS equivalent, and antibiotics (50 units/ml penicillin—50 µg/ml streptomycin or 50 µg/ml gentamycin) to which an appropriate pre-titrated concentration of phytohemagglutinin (PHA) has been added. The primary lymphocytes should be stimulated with PHA for a minimum of two days prior to use in the assay although a three day stimulation is preferable. Before being used for the assay, the PHA-containing medium is removed by centrifugation and the cells are washed once with cell culture medium minus PHA by centrifugation. The cells are resuspended in RPMI 1640 with antibiotics but without FBS for the virus adsorption phase of the assay.

Any HIV or related animal immunodeficiency virus (e.g. simian immunodeficiency virus) can be used in this assay in association with primary lymphocytes obtained from the appropriate species (e.g. rhesus macaque or other non-human primates). The clinical isolates used in the example experiment reported herein had been received in the laboratory and placed in coculture for less than 1 month (301998) and less than 2 months (302050) prior to being used for the neutralization assay. Although this test was developed specifically to evaluate neutralization of primary clinical isolates of HIV, it can also be used for laboratory strains of HIV including, but not limited to, IIIB, MN, SF2, and RF. It is often desirable to test an antibody sample against more than one virus, including multiple primary clinical isolates and at least one laboratory strain. Conversely, it may also be desirable to test a primary clinical HIV isolate against multiple antibody samples including serum samples from HIV-infected or vaccinated individuals and known negative and positive control serum.

Any antibody of interest which reacts with HIV or to the cells that are, or capable of being, infected by HIV can be used in this assay. For example, human or animal sera which contain, or are suspected to contain, anti-HIV antibodies, can be tested. Alternatively, polyclonal or monoclonal antibodies, either alone or in combination can be tested. Purified or unpurified antibodies of the classes IgG, IgA, IgM, IgE, etc. may be tested.

The inventor has surprisingly discovered that if the initial step wherein the antibody sample to be tested and the HIV are preincubated is not performed and if the virus inoculum and antibody are not removed during the culture period following virus adsorption, then the assay is more effective for determining the ability of an antibody sample to neutralize HIV. Ideally, the HIV and antibody sample to be tested are added to the primary human lymphocytes separately but at approximately the same time. However, for simplicity and accuracy in carrying out the test, especially when extremely small volumes of virus and antibody are involved, the antibody sample to be tested and the HIV can be mixed together and immediately added to the primary human lymphocytes. What is unnecessary and possibly detrimental is a significant amount of preincubation of the antibody sample to be tested with the HIV as described in the control comparison experiment reported herein and as described in the above-cited literature references which describe such preincubation.

If the antibody sample and the HIV are pre-mixed prior to adding them to the lymphocytes, they should be mixed under conditions whereby they do not strongly bind to each other. Whether or not they strongly bind to each other will be affected by the length of time that they are mixed or incubated together and other conditions such as the temperature and composition of the medium in which they are mixed. If the antibody and HIV are pre-mixed prior to adding them to the lymphocytes, they will usually be added to the lymphocytes less than 15 minutes, preferably less than 5 minutes, more preferably less than 2 minutes and most preferably less than 1 minute after mixing. In addition, both virus and antibody should be maintained during this manipulation at a temperature less than 6° C. and most preferably 1° to 4° C. Antibodies and virus will be diluted in a physiological solution such as RPMI 1640 without FBS, Hanks Balanced Salt Solution or Dulbecco's phosphate buffered saline.

The antibody sample, virus and cells are combined in a limited volume (e.g. 10–25% of final culture volume) to allow for efficient adsorption of virus to the cells. Ideally, during virus adsorption, the virus-antibody sample-cell mixture should be agitated by continuous gentle mechanical rocking to maintain the cells in suspension and promote virus-cell interaction. However, manual mixing of the virus-antibody sample-cell suspension at 10 minute intervals is also acceptable, if necessary. Virus adsorption should be carried out for a minimum of 45 minutes, preferably for a minimum of 1 hour at about 37° C. in a humidified 5% $CO_2$ atmosphere. This adsorption period may be extended to 2 to 4 hours if desired or considered necessary to promote optimum virus adsorption to and incorporation into the target primary human lymphocytes.

Subsequent to adsorption, the virus-antibody sample-cell mixture is transferred to a cell culture vessel such as a 96-well plate, multi-well dish or flask. Additional culture medium, i.e. RPMI 1640 plus 10% FBS or FBS equivalent, appropriate antibiotics (50 units/ml penicillin—50 µg/ml streptomycin or 50 µg/ml gentamycin), and interleukin-2 (IL-2) at a concentration predetermined to support lymphocyte proliferation are added to a volume optimum for the culture vessel used for the assay. Alternatively, the additional culture medium is added to the cell culture vessel in which the adsorption was carried out.

The infected cells are then grown at 37° C. in a humidified

5% $CO_2$ atmosphere for a period of time to allow for HIV replication, e.g. 2 to 14 days. Division of the infected cultures is preferably avoided during this incubation period; however, additional fresh culture medium may be added, if required.

Virus replication is then determined after a given amount of time or periodically by conventional procedures which indirectly measure virus growth on the basis of the presence of viral proteins such as p24 or reverse transcriptase (RT) in the culture medium or by other techniques known in the art.

Normal human or other animal serum should be used as a negative control in these neutralization assays and one or more known HIV-neutralizing antibodies or sera should be used as a positive control.

The degree of neutralization is determined by comparing the amount of viral protein in culture medium from test samples containing antibody sample with the amount of viral protein in control samples containing virus but no antibody and is expressed as percent neutralization relative to this control. Results ≧90% neutralization are considered indicative of significant neutralization efficacy although results encompassing ≧50% neutralization can be useful for comparative purposes and for classifying and serotyping primary clinical HIV isolates. Neutralization values below 50% are considered to be insignificant and reflective of biological variation within the assay procedure.

EXAMPLE 1

Assay Components

Antibodies (1) HIVIG—serum pool from HIV positive humans
(2) Anti-gp120 mouse monoclonal antibody
(3) FDA 1—serum from HIV positive human
(4) FDA 2—serum from HIV positive human
(5) IVIG—normal human serum pool Viruses (1) Primary HIV isolate 301998 (Pittsburgh early seroconverter) unfiltered PBMC culture medium;
(2) Primary HIV isolate 302050(Thailand late-stage AIDS) filtered PBMC culture medium; and
(3) Laboratory strain $HIV_{IIIB}$ filtered PBMC culture medium Assay Procedure All antibodies were heat inactivated (56° C. for 30 minutes) and diluted 1:5 with RPMI 1640(Quality Biological, Inc.) plus 50 units/ml penicillin—50 µg/ml streptomycin by mixing 25 µl antibody with 100 µl RPMI. After preparation, antibody dilutions were maintained at ≦4° C.

Virus stocks were removed from −80° C. storage, rapidly thawed in a 37° C. water bath, and a 1:2 dilution of each virus was prepared by mixing 0.9 ml of virus stock with 0.9 ml RPMI 1640 plus 50 units/ml penicillin—50 µg/ml streptomycin. A 1:10 dilution of each virus stock was prepared by mixing 0.4 ml of the 1:2 dilution with 1.6 ml of RPMI. After preparation, virus dilutions were maintained at ≦4° C.

$4×10^7$ primary human lymphocytes, stimulated with PHA for 3 days, were centrifuged at 340× g for 5 minutes to pellet and the supernatant culture medium aspirated. The cells were washed with RPMI 1640 plus 50 units/ml penicillin—50 µg/ml streptomycin by centrifugation and the pelleted cells were resuspended in 8 ml of RPMI 1640 plus penicillin—streptomycin to provide a concentration of $5×10^6$ cells/ml or $5×10^5$ cells/100 µl. The cell suspension was held at room temperature.

100 µl of the 1:2 and 1:10 dilution of each virus was added to a series of six microfuge tubes in duplicate. 10 µl of each of the five antibody dilutions was added to the 1:2 and 1:10 dilutions of each virus in duplicate. 10 µl of RPMI 1640 was added to the 1:2 and 1:10 dilution of each virus in duplicate to serve as the reference control consisting of virus without antibody. Tubes containing virus-antibody sample mixture were maintained at ≦4° C. during these additions.

Using a wide bore cell culture pipette tip, 100 µl ($5×10^5$ cells) of the primary human lymphocyte cell suspension was transferred to each microfuge tube. The tubes containing cells, antibody samples and virus were vortexed gently to mix and incubated for 1 hour at 37° C. on a rocker in the 5% $CO_2$ incubator.

Following virus adsorption, each cell-antibody sample-virus mixture was transferred with a wide bore cell culture pipette tip to an individual well of a 24-well tissue culture plate. Each well contained 1.3 ml RPMI 1640 plus 15% FBS, 50 units/ml penicillin—50 µg/ml streptomycin, and 30 units/ml recombinant IL-2 thus resulting in a final total culture volume of 1.5 ml. The 24-well plates were incubated at 37° C. in a 5% humidified $CO_2$ atmosphere for 8 days.

On days 4, 6, and 8 post infection (PI), 100 µl samples of culture medium were removed from each well and transferred to a 96-well plate. These samples were stored at −20° C. until assayed for HIV reverse transcriptase using a non-radioactive RT assay (Boehringer Mannheim) according to instructions provided by the manufacturer.

Assay Results

The neutralization results from day 8 PI are shown below. Day 4 and 6 PI neutralization results are comparable.

| | HIV 301998 | | | |
|---|---|---|---|---|
| | 1:2 | | 1:10 | |
| | pg RT/0.1 ml | % Neutralization | pg RT/0.1 ml | % Neutralization |
| Control | 138.8 ± 1.6 | — | 62.6 ± 15.5 | — |
| IVIG | 128.7 ± 21.4 | 7.3 | 23.2 ± 3.0 | 62.9 |
| HIVIG | 17.3 ± 4.2 | 87.5 | 4.6 ± 0.3 | 92.6 |
| gp120 MAb | 164.1 ± 8.7 | 0 | 63.0 ± 17.6 | 0 |
| FDA 1 | 67.9 ± 18.1 | 51.1 | 12.0 ± 7.3 | 80.8 |
| FDA 2 | 70.2 ± 0.9 | 49.4 | 15.9 ± 9.8 | 74.6 |

| | HIV 302050 | | | |
|---|---|---|---|---|
| | 1:2 | | 1:10 | |
| | pg RT/0.1 ml | % Neutralization | pg RT/0.1 ml | % Neutralization |
| Control | 164.2 ± 4.3 | — | 50.2 ± 13.0 | — |
| IVIG | 93.6 ± 4.5 | 43.0 | 46.1 ± 13.9 | 8.2 |
| HIVIG | 14.2 ± 0.9 | 91.4 | 4.5 ± 0.0 | 91.0 |
| gp120 MAb | 150.7 ± 0.3 | 8.2 | 79.4 ± 3.3 | 0 |
| FDA 1 | 76.1 ± 7.4 | 53.6 | 27.7 ± 7.7 | 44.8 |

-continued

| | HIV 302050 | | | |
|---|---|---|---|---|
| | 1:2 | | 1:10 | |
| | pg RT/0.1 ml | % Neutralization | pg RT/0.1 ml | % Neutralization |
| FDA 2 | 47.3 ± 10.6 | 71.2 | 15.2 ± 4.2 | 69.7 |

| | HIV$_{IIIB}$ | | | |
|---|---|---|---|---|
| | 1:2 | | 1:10 | |
| | pg RT/0.1 ml | % Neutralization | pg RT/0.1 ml | % Neutralization |
| Control | 123.0 ± 11.5 | — | 93.5 ± 4.2 | — |
| IVIG | 117.9 ± 33.6 | 4.1 | 83.9 ± 1.2 | 10.3 |
| HIVIG | 6.6 ± 0.6 | 94.6 | 2.6 ± 1.0 | 97.2 |
| gp120 MAb | 122.7 ± 7.0 | 0.2 | 114.7 ± 14.4 | 0 |
| FDA 1 | 37.2 ± 7.1 | 69.8 | 15.9 ± 5.7 | 83.0 |
| FDA 2 | 33.8 ± 9.1 | 72.5 | 11.4 ± 1.4 | 87.8 |

EXAMPLE 2: COMPARATIVE ASSAY

Assay Components

Antibodies (1) HIVIG—serum pool from HIV positive humans
(2) Anti-gp120 mouse monoclonal antibody
(3) FDA 1—serum from HIV positive human
(4) FDA 2—serum from HIV positive human
(5) IVIG—normal human serum pool Viruses (1) Primary HIV isolate 301998 (Pittsburgh early seroconverter) unfiltered PBMC culture medium;
(2) Primary HIV isolate 302050 (Thailand late-stage AIDS) filtered PBMC culture medium; and
(3) Laboratory strain HIV$_{IIIB}$ filtered PBMC culture medium Assay Procedure All antibodies were heat inactivated (56° C. for 30 minutes) and diluted 1:5 as described in Example 1.

Virus stocks were thawed and diluted 1:2 and 1:10 as described in Example 1.

$1.3×10^8$ primary human lymphocytes, stimulated with PHA for 2 days, were prepared for use in the experiment as described in Example 1.

One entire neutralization assay was carried out exactly as described in Example 1 with the following modifications: 1) use of $8×10^5$ rather than $5×10^5$ cells per well; 2) removal of culture medium samples for assay on days 5, 7, and 12 PI rather than 4, 6, and 8. This assay procedure will be designated as Innovation.

Simultaneously, a second neutralization assay, designated Conventional, was carried out using the established procedure involving preincubation of virus and antibody sample and removal of the excess virus inoculum and antibody following virus adsorption as described below.

100 μl of the 1:2 and 1:10 dilution of each virus was added to a series of six microfuge tubes in duplicate. 10 μl of each of the five antibody dilutions was added to the 1:2 and 1:10 dilutions of each virus in duplicate. 10 μl of RPMI 1640 was added to the 1:2 and 1:10 dilution of each virus in duplicate to serve as the reference control consisting of virus without antibody. Tubes containing virus-antibody sample mixture were mixed by gentle vortexing and incubated for 1 hour at 37° C. on a rocker in the 5% $CO_2$ incubator. Following virus adsorption, 0.8 ml RPMI 1640 plus antibiotics was added to each tube and the contents mixed by gentle vortexing. The tubes were centrifuged for 1 minute in a microfuge to pellet the cells and the culture medium was aspirated. To wash, 1 ml of RPMI 1640 plus antibiotics was added to each tube, the pelleted cells were resuspended and mixed by gentle vortexing, and the tubes were centrifuged for 1 minute in a microfuge. The culture medium was aspirated and the cell pellet was resuspended in 0.75 ml RPMI 1640 plus 15% FBS, 50 units/ml penicillin—50 μg/ml streptomycin, and 30 units/ml recombinant IL-2. Each cell-antibody sample-virus mixture was transferred with a wide bore cell culture pipette tip to an individual well of a 24-well tissue culture plate. Each well contained 0.75 ml RPMI 1640 plus 15% FBS, penicillin—streptomycin, and 30 units/ml recombinant IL-2 thus resulting in a final total culture volume of 1.5 ml. The 24-well plates were incubated at 37° C. in a 5% humidified $CO_2$ atmosphere for 8 days.

Using a wide bore cell culture pipette tip, 100 μl ($8×10^5$ cells) of the primary human lymphocyte cell suspension was transferred to each microfuge tube. The tubes containing cells, antibody samples and virus were vortexed gently to mix and incubated for an additional 1 hour at 37° C. on a rocker in the 5% $CO_2$ incubator. Following virus adsorption, each cell-antibody sample-virus mixture was transferred with a wide bore cell culture pipette tip to an individual well of a 24-well tissue culture plate. Each well contained 1.3 ml RPMI 1640 plus 10% FBS, penicillin—streptomycin, and 30 units/ml recombinant IL-2 thus resulting in a final total culture volume of 1.5 ml. The 24-well plates were incubated at 37° C. in a 5% humidified $CO^2$ atmosphere for 8 days.

On days 5, 7, and 12 PI, 100 μl samples of culture medium were removed from each well and transferred to a 96-well plate. These samples were stored at −20° C. until assayed for HIV reverse transcriptase using a non-radioactive RT assay (Boehringer Mannhelm) according to instructions provided by the manufacturer.

Assay Results

Neutralization results obtained on day 12 after infection with a 1:2 dilution of each virus are shown below. These results are representative of those obtained at the two other sample times and those obtained with the 1:10 dilution of virus.

| | HIV 301998 | | | |
|---|---|---|---|---|
| | Innovation | | Conventional | |
| | pg RT/0.1 ml | % Neutralization | pg RT/0.1 ml | % Neutralization |
| Control | 85.5 ± 0.5 | — | 70.8 ± 5.8 | — |
| IVIG | 136.3 ± 24.3 | 0 | 87.9 ± 0.8 | 0 |

-continued

HIV 301998

| | Innovation | | Conventional | |
|---|---|---|---|---|
| | pg RT/0.1 ml | % Neutralization | pg RT/0.1 ml | % Neutralization |
| HIVIG | 29.4 ± 6.1 | 65.6 | 125.2 ± 10.7 | 0 |
| gp120 MAb | 134.4 ± 16.9 | 0 | 118.0 ± 19.4 | 0 |
| FDA 1 | 82.2 ± 22.5 | 3.8 | 78.7 ± 0 | 0 |
| FDA 2 | 121.7 ± 6.6 | 0 | 89.2 ± 4.6 | 0 |

HIV 302050

| | Innovation | | Conventional | |
|---|---|---|---|---|
| | pg RT/0.1 ml | % Neutralization | pg RT/0.1 ml | % Neutralization |
| Control | 34.8 ± 23.9 | — | 16.7 ± 2.0 | — |
| IVIG | 29.3 ± 0.8 | 15.8 | 38.9 ± 11.3 | 0 |
| HIVIG | 2.5 ± 1.4 | 92.8 | 15.9 ± 0.1 | 4.8 |
| gp120 MAb | 36.3 ± 8.0 | 0 | 10.7 ± 1.3 | 35.9 |
| FDA 1 | 18.6 ± 4.7 | 46.6 | 16.1 ± 1.7 | 3.6 |
| FDA2 | 15.2 ± 3.2 | 56.3 | 16.0 ± 0.2 | 4.2 |

$HIV_{IIIB}$

| | Innovation | | Conventional | |
|---|---|---|---|---|
| | pg RT/0.1 ml | % Neutralization | pg RT/0.1 ml | % Neutralization |
| Control | 84.2 ± 0.1 | — | 71.4 ± 0.5 | — |
| IVIG | 99.2 ± 31.0 | 0 | 84.5 ± 13.0 | 0 |
| HIVIG | 4.7 ± 1.7 | 94.4 | 120.6 ± 33.8 | 0 |
| gp120 MAb | 116.5 ± 4.7 | 0 | 124.5 ± 34.9 | 0 |
| FDA 1 | 32.3 ± 8.2 | 61.6 | 105.0 ± 26.0 | 0 |
| FDA 2 | 55.2 ± 9.6 | 34.4 | 68.3 ± 18.0 | 4.3 |

What is claimed is:

1. An immunodeficiency virus neutralization assay, comprising the steps of:
   contacting human lymphocytes with human immunodeficiency virus type 1(HIV-1) and an antibody, with or without premixing of said HIV-1 and said antibody, wherein if said HIV-1 and said antibody are mixed together, the mixture is added to said human lymphocytes less than fifteen minutes after mixing;
   culturing said human lymphocytes under conditions which allow for HIV-1 replication; and
   measuring HIV-1 replication in said human lymphocytes.

2. The assay of claim 1, which is an assay to determine the ability of an antibody in an unknown serum sample to neutralize HIV-1 which comprises the steps of:
   contacting primary human lymphocytes with HIV-1 and an unknown serum sample to be tested;
   culturing said primary human lymphocytes under conditions which allow for HIV-1 replication; and
   measuring HIV-1 replication in said primary human lymphocytes.

3. The assay of claim 1, which is an assay to identify or serotype an unknown HIV-1 isolate which comprises the steps of:
   contacting primary human lymphocytes with said HIV-1 and a known antibody, with or without premixing of said HIV-1 and said antibody, wherein if said HIV-1 and said antibody are mixed together, the mixture is added to said primary human lymphocytes less than fifteen minutes after mixing;
   culturing said primary human lymphocytes under conditions which allow for HIV-1 replication; and
   measuring HIV-1 replication in said primary human lymphocytes.

4. The assay of claim 1, wherein said HIV-1 and said antibody are mixed together for less than fifteen minutes before adding the mixture to primary human lymphocytes.

5. The assay of claim 1, wherein said HIV-1 and said antibody are mixed together prior to adding the mixture to primary human lymphocytes and said mixture is maintained at a temperature less than 6° C. until the mixture is added to said primary human lymphocytes.

6. The assay of claim 1, wherein said HIV-1 is a primary HIV clinical isolate.

7. The assay of claim 1, wherein there is no removal of HIV-1 inoculum and antibody during the assay.

8. The assay of claim 1, 2 or 3, wherein said HIV-1 and said antibody are added to human lymphocytes at approximately the same time.

9. The assay of claim 1, 2 or 3, wherein said HIV-1 and said antibody are mixed together and then added to human lymphocytes.

10. The assay of claim 1, wherein a mixture of virus and antibody is maintained at a temperature of less than 6° C. before adding the mixture to said human lympocytes.

11. The assay of claim 1, wherein a mixture of virus and antibody is maintained at a temperature of 1 to 4° C. before adding the mixture to said human lymphocytes.

12. The assay of claim 1, wherein viral replication is measured by measuring the presence of HIV-1 proteins.

13. A human immunodeficiency virus type 1(HIV-1) neutralization assay, comprising the steps of:
   mixing HIV-1 and an antibody together and maintaining the resulting mixture at a temperature less than 6° C. and for a time of less than 15 minutes;
   contacting primary human lymphocytes with the mixture of HIV-1 and an antibody for at least 45 minutes to allow for adsorption between said primary human lymphocytes, said HIV-1 and antibody;
   culturing said primary human lymphocytes under conditions which allow for HIV-1 replication, without washing said primary human lymphocytes; and
   measuring HIV-1 replication in said primary human lymphocytes.

14. An assay for determining the ability of an antibody sample to neutralize primary clinical isolates of human immunodeficiency virus type 1(HIV-1) which comprises the steps of:
   contacting primary human lymphocytes with HIV-1 and an antibody sample to be tested with or without premixing of said HIV-1 and said antibody wherein if said HIV-1 and said antibody are mixed together, the mixture is added to said primary human lymphocytes less than fifteen minutes after mixing;
   culturing the primary human lymphocytes in the continuous presence of both the virus inoculum and the antibody sample to be tested under conditions which allow for HIV-1 replication; and measuring HIV-1 replication in the primary human lymphocytes.

15. A method for assaying the ability of an antibody to neutralize primary clinical isolates of the human immunodeficiency virus type 1 (HIV-1), as well as laboratory strains of the virus, in primary human lymphocytes, comprising the steps of:

contacting primary human lymphocytes with HIV-1 and an antibody sample to be tested with or without pre-mixing of said HIV-1 and said antibody wherein if said HIV-1 and said antibody are mixed together, the mixture is added to said primary human lymphocytes less than fifteen minutes after mixing;

culturing said primary human lymphocytes under conditions which allow for HIV-1 replication without removal of the unadsorbed virus inoculum or unreacted antibody being tested; and measuring HIV-1 replication in said primary human lymphocytes.

16. A human immunodeficiency virus type 1(HIV-1) neutralization assay, comprising the steps of:

mixing HIV-1 and an antibody and maintaining the mixture at a temperature less than 6° C. until the mixture is contacted with human lymphocytes;

contacting human lymphocytes with said mixture of HIV-1 and an antibody;

culturing said human lymphocytes under conditions which allow for HIV-1 replication; and measuring HIV-1 replication in said human lymphocytes.

17. The assay of claim 16, wherein the mixture is added to human lymphocytes less than 5 minutes after mixing.

18. The assay of claim 16, wherein the mixture is added to human lymphocytes less than 2 minutes after mixing.

19. The assay of claim 16, wherein the mixture is added to human lymphocytes less than 1 minute after mixing.

* * * * *